United States Patent
Carr et al.

(10) Patent No.: US 8,384,891 B2
(45) Date of Patent: Feb. 26, 2013

(54) DIRECT DETECTION OF MARKERS IN PRESSURIZED HYDROCARBON FLUIDS

(75) Inventors: Paul Carr, Yorkshire (GB); Ian Eastwood, Lancashire (GB); Iain Webster, Cleveland (GB)

(73) Assignee: Authentix, Inc., Addison, TX (US)

( * ) Notice: Subject to any disclaimer, the term of this patent is extended or adjusted under 35 U.S.C. 154(b) by 368 days.

(21) Appl. No.: 12/670,957

(22) PCT Filed: Aug. 2, 2007

(86) PCT No.: PCT/US2007/075081
§ 371 (c)(1),
(2), (4) Date: Jan. 27, 2010

(87) PCT Pub. No.: WO2009/017505
PCT Pub. Date: Feb. 5, 2009

(65) Prior Publication Data
US 2010/0208260 A1    Aug. 19, 2010

(51) Int. Cl.
*G01J 3/00* (2006.01)
(52) U.S. Cl. .................................. 356/300; 356/326
(58) Field of Classification Search .................. 356/300, 356/303, 326
See application file for complete search history.

(56) References Cited

U.S. PATENT DOCUMENTS

| | | |
|---|---|---|
| 4,551,154 A | 11/1985 | Malcosky et al. |
| 5,928,954 A | 7/1999 | Rutledge et al. |
| 7,208,451 B2 | 4/2007 | Spall et al. |
| 7,258,098 B2 * | 8/2007 | Kim ........................... 123/198 D |
| 2004/0147413 A1 | 7/2004 | Spall et al. |
| 2006/0000261 A1 * | 1/2006 | Wardlaw, III .................. 73/40.7 |

FOREIGN PATENT DOCUMENTS

| | | |
|---|---|---|
| EP | 1126263 A | 8/2001 |
| WO | 01/22087 A | 3/2001 |

OTHER PUBLICATIONS

European Patent Office (ISA/EP); Written Opinion of the International Searching Authority for PCT/US2007/075081; Apr. 16, 2008; Rijswijk, NL.
Written Opinion of the International Searching Authority, PCT/US07/75081, 5 pages, 2010.

* cited by examiner

*Primary Examiner* — Layla Lauchman
(74) *Attorney, Agent, or Firm* — Kelly Kordzik; Matheson Keys & Kordzik PLLC

(57) ABSTRACT

This invention generally relates to a method and apparatus for direct detection of one or more markers in pressurized hydrocarbon fluids. The apparatus includes a vessel (130) and one or more valves (150, 160, 170). The hydrocarbon fluid (240) may be a liquid or gas. Markers may include a variety of optical markers, such as fluorescent markers. The apparatus may be coupled to a hydrocarbon fluid source (210), and the vessel (130) may be at least partially filled with hydrocarbon fluid from the hydrocarbon fluid source (210). A> detector (140) coupled to the vessel (130) may be used to detect at least one of the markers in the hydrocarbon fluid (240) while the apparatus is coupled to the hydrocarbon fluid source (210) and without the addition of reagents. Detection of markers may include, for example, fluorescence detection.

44 Claims, 1 Drawing Sheet

DIRECT DETECTION OF MARKERS IN PRESSURIZED HYDROCARBON FLUIDS

TECHNICAL FIELD

This invention generally relates to a method and apparatus for direct detection of one or more markers in pressurized hydrocarbon fluids.

BACKGROUND INFORMATION

Petroleum products are subject to adulteration and tax evasion worldwide. These illegal practices deprive governments and legitimate businesses of profits and may be hazardous to users, as well as the environment. Such deception can also cause harm, sometimes irreparable harm, including, for example, to the brand name or brand image of the producer of the original product. Significant commercial gain can also be obtained by counterfeiters through the dilution of the original products with a readily available, less expensive material. Markers for petroleum products that provide a technique to determine the authenticity of the product are known in the art. For instance, petroleum products can be tagged for identification purposes with coloring agents to provide a distinct color visually perceptible to the naked eye.

Unlike most hydrocarbon fuels, liquefied petroleum gas (LPG) is stored in a liquid form and used in a gaseous form. When an outlet valve on an LPG source (for example, a tank or cylinder) is opened, gas pressure from the liquid in the source causes gas to flow without a pump. Pressure requirements for different applications may be met by use of an appropriate pressure regulator with the source.

LPG may be sold as bottled gas or delivered to and stored in above-ground or below-ground tanks for use in households, road transportation, industry, agriculture, and the energy sector. The relatively low price of LPG has resulted in increased usage of this fuel for engines. Suppliers that do not pay required taxes offer cost advantages through unfair practices, without necessarily adhering to safety and maintenance standards. In some cases, bottled gas cylinders are refilled illegally, increasing the risk of explosion.

Various actions have been taken to counteract these illegal practices. In some cases, security features for LPG cylinders are implemented to reduce counterfeiting of these cylinders. In other cases, markers are added to LPG at relatively high ppm levels to indicate, for example, an origin or intended use of the LPG. This high marker concentration can lead to fouling of nozzles and injection systems. The markers may include, for example, fluorescent material. Conventional sampling methods generally involve removing a sample of the hydrocarbon fluid and testing for the presence of a marker to authenticate the source of the hydrocarbon fluid.

SUMMARY

Embodiments of the present invention relate to a method and apparatus for detecting a marker in a pressurized hydrocarbon fluid. In general, in one aspect, an apparatus includes a first valve configured to be coupled to a hydrocarbon fluid source, a vessel coupled to the first valve, and a detector configured to be coupled to the vessel. The first valve is configured to allow pressurized hydrocarbon fluid from the hydrocarbon fluid source to flow into the vessel, and the detector is operable to detect a property of the marker in the pressurized hydrocarbon fluid in the vessel during use.

Implementations of the invention may include one or more of the following features. The apparatus may allow direct detection of the marker in the pressurized hydrocarbon fluid. The apparatus may allow direct detection of the marker in the pressurized hydrocarbon fluid using an in-line optical fiber. The pressurized hydrocarbon fluid may be liquefied petroleum gas. The first valve is configured to be coupled to a processor or is coupled to a processor. In some embodiments, the apparatus includes a second valve. The second valve is coupled to the first valve, and allows the pressurized hydrocarbon fluid to be released from the apparatus in a liquid or a gaseous state. In some embodiments, the apparatus includes a third valve. The third valve is coupled to the vessel, and is configured to allow the pressurized hydrocarbon fluid to be released from the apparatus in a gaseous state. In some embodiments, the vessel is configured to contain a pressurized hydrocarbon fluid at a pressure of up to about 15 bar. The detector may be configured to be operatively or physically coupled to the vessel. In some embodiments, the detector includes a spectrometer. The detector may include a fluorometer.

In another aspect, the invention features a system including a hydrocarbon fluid source with a pressurized hydrocarbon fluid with a marker, a first valve configured to be coupled to the hydrocarbon fluid source, a vessel coupled to the first valve, and a detector configured to be coupled to the vessel. The first valve is configured to allow at least some of the pressurized hydrocarbon fluid in the hydrocarbon fluid source to flow into the vessel, and the detector is operable to detect a property of the marker in the pressurized hydrocarbon fluid in the vessel during use.

Implementations of the invention may include one or more of the following features. The first valve may be coupled to the hydrocarbon fluid source. The detector may be coupled to the vessel. In some embodiments, the detector includes a spectrometer. The detector may be a fluorometer. The system may include a processor, and the processor may be coupled to the detector and/or to the first valve. The system may allow direct detection of the marker in the pressurized hydrocarbon fluid.

In another aspect, the invention features an apparatus for detecting a marker in a pressurized hydrocarbon fluid. The apparatus includes a first valve configured to be coupled to a hydrocarbon fluid source and a vessel coupled to the first valve. The first valve is configured to allow pressurized hydrocarbon fluid from the hydrocarbon fluid source to flow into the vessel, and the vessel is configured to be coupled to a detector to allow direct detection of a property of the marker in the pressurized hydrocarbon fluid. The apparatus may allow direct detection of the marker in the pressurized hydrocarbon fluid using an in-line optical fiber. The detector may be operatively or physically coupled to the vessel.

In another aspect, the invention features a method of detecting a marker in a pressurized hydrocarbon fluid. The method includes coupling a to a hydrocarbon fluid source with a pressurized hydrocarbon fluid, at least partially filling the vessel with the pressurized hydrocarbon fluid from the hydrocarbon fluid source, and detecting a property the marker in the hydrocarbon fluid with a detector while the vessel is coupled to the hydrocarbon fluid.

Implementations of the invention may include one or more of the following features. At least partially filling the vessel may include purging air from the vessel. Detecting may include coupling the detector to the vessel and/or assessing an amount of the marker in the pressurized hydrocarbon fluid. In some embodiments, the detector includes a light source, and detecting includes illuminating the pressurized hydrocarbon fluid in the vessel with the light source. The detector may include a fluorometer. In some embodiments, at least partially filling the vessel includes controlling a valve coupled to the hydrocarbon fluid source with a processor. Detecting the property of the marker in the pressurized hydrocarbon fluid with a detector may include controlling the detector with a processor. The method may further include decoupling the vessel from the hydrocarbon fluid source.

In further embodiments, features from specific embodiments may be combined with features from other embodiments. For example, features from one embodiment may be combined with features from any of the other embodiments. In further embodiments, additional features may be added to the specific embodiments described herein.

DETAILED DESCRIPTION OF THE DRAWINGS

Advantages of the present invention will become more apparent from the detailed description given hereinafter. However, it should be understood that the detailed description and specific examples, while indicating certain embodiments of the invention, are given by way of illustration only, since various changes and modifications within the spirit and scope of the invention will become apparent to those skilled in the art from this detailed description.

Figure 1:
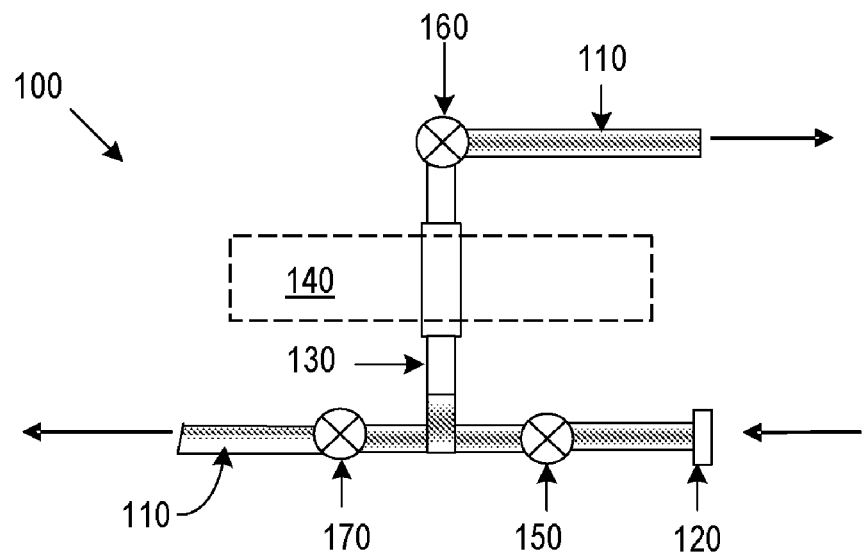
FIG. 1 is a schematic diagram depicting an embodiment of an apparatus for direct detection of one or more markers in a hydrocarbon fluid.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

The following terms shall have the definitions given below when used in either lower case or with capitalizations in this specification:

As used herein, "authenticate" generally refers to confirm a product or commodity as genuine or substantially unadulterated or to confirm an origin or intended use of a product or commodity.

As used herein, "coupled" generally refers to pieces that may be used operatively with each other, or pieces that are joined or linked together, with or without one or more intervening members. As described herein, pieces that are coupled may be removably coupled. That is, coupled pieces may be uncoupled to alter a relationship between the coupled pieces. Pieces that are physically coupled are in direct contact.

As used herein, "direct detection" generally refers to a process in which one or more markers are detected in a hydrocarbon fluid in an apparatus that is coupled to the hydrocarbon fluid source and, generally, without the addition of reagents to the hydrocarbon fluid. Thus, detection of markers may be achieved at the site of the hydrocarbon fluid source.

As used herein, "detector" generally refers to an apparatus or system used to detect the presence of an object, radiation, chemical compound, or such. A detector may be, for instance, a fluorometer. A detector may have a radiation source. The radiation source may provide electromagnetic radiation of one wavelength or a range of wavelengths including, but not limited to, visible, ultraviolet, and infrared radiation or a combination thereof.

As used herein, "fluorometer" generally refers to an instrument that irradiates a sample and measures the fluorescent radiation emitted by the sample that is exposed to radiation. A fluorometer may provide the intensity of the radiation producing fluorescence.

As used herein, "hydrocarbon fluid" generally refers to an aggregate of matter consisting essentially of carbon and hydrogen in which the molecules are able to flow past each other without limit and without fracture planes forming. A hydrocarbon fluid may be, for instance, a liquid or a gas. A hydrocarbon liquid may be formed by pressurizing a hydrocarbon gas. Hydrocarbon fluids include, but are not limited to, fuels, oils, lubricants, and other petroleum products. A hydrocarbon fluid source may be a container of any description that contains hydrocarbon fluid or a conduit of any description that allows the passage of a hydrocarbon fluid.

As used herein, "liquefied natural gas" or "LNG" is natural gas generally known to include a high percentage of methane, but also other elements and/or compounds including, but not limited to, ethane, propane, butane, carbon dioxide, nitrogen, helium, hydrogen sulfide, or combinations thereof) that has been processed to remove one or more components (for instance, helium) or impurities (for instance, water and/or heavy hydrocarbons) and then condensed into a liquid at almost atmospheric pressure by cooling.

As used herein, "liquefied petroleum gas" or "LPG" generally refers to a mixture of propane, butane, and other light hydrocarbons derived from refining crude oil. At normal temperature this mixture is a gas but can be cooled or subjected to pressure to facilitate storage and transportation.

As used herein, "marker" generally refers to a material used to authenticate or identify a hydrocarbon fluid by absorbing, reflecting, emitting, or otherwise altering electromagnetic radiation incident on the marker. Light-emitting markers may exhibit phosphorescence, chemiluminescence, electroluminescence, fluorescence upconversion, Raman fluorescence, or fluorescence alone or in combination with the hydrocarbon fluid. A marker may respond to incident electromagnetic radiation so as to change in a physically measurable manner upon exposure to one or more wavelengths of light. As used herein, marker generally refers to one or more markers.

As used herein, "processor" generally refers to an electronic device that receives, processes, and outputs data.

As used herein, "vessel" generally refers to a vessel that permits passage of radiation of interest from an exterior of the vessel to an interior of the vessel. The vessel may be, for instance, a conduit or a container, such as a cuvette or a flow cell. The vessel may be transparent, translucent, or opaque.

The apparatus and methods described below are applicable to a wide range of hydrocarbon fluids and may be used to authenticate these fluids in a range of circumstances.

When selecting a marker to be added to a hydrocarbon fluid, the marker is desirably immune to extraction from the hydrocarbon fluid by common means. By common means, it is meant that the marker cannot be substantially differentially adsorbed from the product using conventional inexpensive adsorbents, cannot be removed by extraction with acids, bases, or immiscible solvents, cannot be easily oxidized, reduced or reacted with common agents to effectively remove them, and the marker should be difficult to disguise by masking with other agents.

Markers added to hydrocarbon fluids may allow qualitative and/or quantitative authentication of the hydrocarbon fluids.

Desirable markers exhibit one or more properties such as adequate solubility in the chosen hydrocarbon fluid, strong absorbance in the region of the radiation provided and minimal absorbance in other regions, strong fluorescence in a chosen wavelength range, and good stability under a range of environmental conditions. Markers that may be added to hydrocarbon fluids include, but are not limited to, visible dyes, such as anthraquinone and diazo dyes, and near infrared dyes, such as squairaines, phthalocyanines, naphthalocyanines, croconic acid derivatives, and pyrazinoporphyrazine dyes. Other markers may include carbonyl compounds, such as ketones, aldehydes, esters, amides, anhydrides and carboxylic acids, which absorb in the infrared. Other markers, such as nonylphenol and Bisphenol A, may include polyamines and/or isocyanates. Markers are available, for example, from Morton International, Inc. (Chicago, Ill.).

After the marker has been selected, it is added to the hydrocarbon fluid. The hydrocarbon fluid may be contained in a transport container such as a tanker truck, tanker ship, pipeline, or any other process known in the art for transporting hydrocarbon fluids from one place to another. For example, and not by way of limitation, if the hydrocarbon fluid is in a pipeline, the marker may be injected into the stream through an injection valve, as the hydrocarbon fluid flows from, for instance, a processing plant to a storage container. If the hydrocarbon fluid is in a tanker truck or ship, the marker may be added by opening a port to the transport container and adding the marker directly through the port. Also, the marker may be injected into the transport container below the fluid level. The hydrocarbon fluid may also be in a static storage container (either above ground or below ground) or a moveable cylinder. If the hydrocarbon fluid is in a static storage container, the marker may be added by opening a port to the static container and adding the marker directly through the port or the marker may be injected into the container below the fluid level. The marker may also be added to a dry container before the hydrocarbon fluid is added. In some embodiments, one or more markers may be dosed into a hydrocarbon fluid along with another additive such as, for example, a sulfur-containing compound.

The amount of marker to be added is based on the properties of the marker and the detection limits of the detector. In some embodiments, the marker may be added in such an amount so the concentration of the marker in the hydrocarbon fluid is in a range of about 0.1 ppb to about 1000 ppm. In other embodiments, the concentration of the marker in the hydrocarbon fluid may be in a range of about 0.1 ppb to about 100 ppm or further in a range of about 1 ppb to about 100 ppb. Markers are chosen to be soluble in the hydrocarbon fluid, such that a concentration of the marker in the hydrocarbon fluid is dispersed substantially uniformly throughout the hydrocarbon fluid. Markers and concentrations thereof are also chosen such that valves, diaphragms, filters, or other portions of a container or equipment contacted by the hydrocarbon fluid are not adversely affected by the marker or the combination of the marker and the hydrocarbon fluid.

Direct detection allows testing of the hydrocarbon fluid to be performed in the field. It is to be understood that testing in the field includes testing at any location where a hydrocarbon fluid source is found. Field determination of the presence of a marker in a hydrocarbon fluid allows rapid qualitative and/or quantitative assessment of one or more properties of the marker. Thus, a hydrocarbon fluid may be authenticated without the necessity of removing a sample of the hydrocarbon fluid from the hydrocarbon fluid source, placing the sample in a container, and transporting the container to another site (for instance, a laboratory) for analysis. Furthermore, direct detection may also allow for the qualitative and/or quantitative assessment of at least one property of a marker without addition of reagents to the hydrocarbon fluid, thereby reducing costs and increasing the efficiency of marker detection. In some embodiments, direct detection includes using an in-line optical fiber, for example, in an substantially opaque vessel for continuous monitoring.

A schematic diagram of an embodiment of an apparatus for direct detection of markers in a hydrocarbon fluid is depicted in FIG. 1. Apparatus 100 includes conduit 110. Conduit 110 may be formed from a material that may include, but is not limited to, stainless steel, resistant plastics, etc., or a combination thereof. Conduit 110 may include two or more conduits coupled together. Conduit 110 may be formed from portions of like or different shapes, sizes (length and/or diameter), and/or composition. In some embodiments, a portion of conduit 110 may be a flexible tubing.

Connector 120 may be directly or indirectly coupled to conduit 110. Connector 120 may include, but is not limited to, a ¼ inch USP connector. Connector 120 may be one of a variety of connectors known in the art to allow apparatus 100 to be coupled a hydrocarbon fluid source. Vessel 130 may be coupled to conduit 110, such as shown in FIG. 1. Vessel 130 may be transparent, translucent, or opaque. Detector 140 may be operatively coupled to vessel 130. Valves 150, 160, 170 may be coupled to conduit 110 to regulate fluid flow into and out of vessel 130.

Vessel 130, when transparent, is designed to allow radiation from detector 140 to pass into the hydrocarbon fluid. The radiation may be any form of electromagnetic radiation including, but not limited to, visible, infrared, and/or ultraviolet radiation. Vessel 130, when transparent, is further designed to allow radiation (emitted from one or more markers in the hydrocarbon fluid in the vessel) to pass through the vessel such that the radiation emitted from the markers may be detected by detector 140.

Vessel 130 may be of any shape, size, or composition known in the art. For instance, vessel 130 may include a rectangular quartz cuvette coupled to conduit 110 with high pressure seals. In one example, vessel 130 is a 10 mm outer diameter glass tube with threaded ends. Conduit 110 may be coupled to two sides of vessel 130 with threaded caps and o-ring seals to allow entry and exit of fluid without leakage. In some embodiments, vessel 130 may be positioned in a housing that secures the threaded caps. For example, a suitable high pressure seal may be able to contain hydrocarbon liquid at a pressure of up to 15 bar at a temperature of 50° C. In some embodiments, vessel 130 may be designed to accept an in-line optical fiber to allow continuous monitoring of fluid in the vessel. In this case, vessel 130 may be opaque.

Detector 140 may be designed to emit and/or collect radiation at one or more wavelengths or one or more ranges of wavelengths. Detector 140 may further be designed to allow data capture and transfer to a receiving device such as, for example, a personal digital assistant, a laptop, or other computer, such that qualitative and/or quantitative assessment of one or more properties of one or more markers in a hydrocarbon fluid may be analyzed, displayed, and/or recorded.

In some embodiments, detector 140 includes a spectrometer capable of monitoring marked LPG at wavelengths where there is low spectral response from unmarked LPG. Detector 140 may include a UV, visible, or infrared spectromter, or a combination thereof. Detector 140 may include a fluorometer. For instance, detector 140 may include a handheld fluorometer available, for instance, from Turner Designs (Sunnyvale, Calif.). In some embodiments, detector 140 may be designed to accept vessel 130 of a desired size and shape.

Optionally, detector 140 may be physically coupled to vessel 130 during use to assess one or more properties of one or more markers in a hydrocarbon fluid. For example, at least a portion of vessel 130 may fit in an opening of detector 140 during use. In some embodiments, detector 140 may be operatively coupled to vessel 130 while being maintained in proximity to the vessel during use without physically contacting the vessel or conduit 110. For example, detector 140 may be a hand-held device, portions of which can be positioned as desired to substantially surround vessel 130. In other embodiments, detector 140 may include, for example, a housing designed to allow the detector to be snap-fit or otherwise removably coupled to conduit 110 such that the detector contacts the conduit and/or vessel 130 during use. In still further embodiments, detector 140 may be affixed to conduit 110 and/or vessel 130 during use.

Detector 140 may be used to detect one or more properties of a hydrocarbon fluid with one or more markers in a vessel 130 including, but not limited to, emission and/or absorbance of radiation. For example, if detector 140 includes a fluorometer, a marker may absorb incident radiation and emit radiation of the same or longer wavelength on the order of nanoseconds. The intensity of the reemitted radiation may be substantially directly proportional to the concentration of the marker in the hydrocarbon fluid. In some embodiments, a detector may be able to detect relative concentrations of two or more markers. Therefore, more than one marker may be added to identify a hydrocarbon fluid. For example, two markers that fluoresce at different wavelengths may be added to a hydrocarbon fluid, and detector 140 may be used to assess a relative concentration of the two markers.

Valves 150, 160, 170 may be any like or different valves known in the art for use with hydrocarbon fluids. First valve 150 may be used to regulate flow of hydrocarbon fluid from the hydrocarbon fluid source to vessel 130. Second valve 160 may be used to vent air and hydrocarbon gas from apparatus 100. Third valve 170 may be used to vent hydrocarbon liquid from apparatus 100. Valves 150, 160, 170 may be operated manually and/or automatically.

Figure 2:
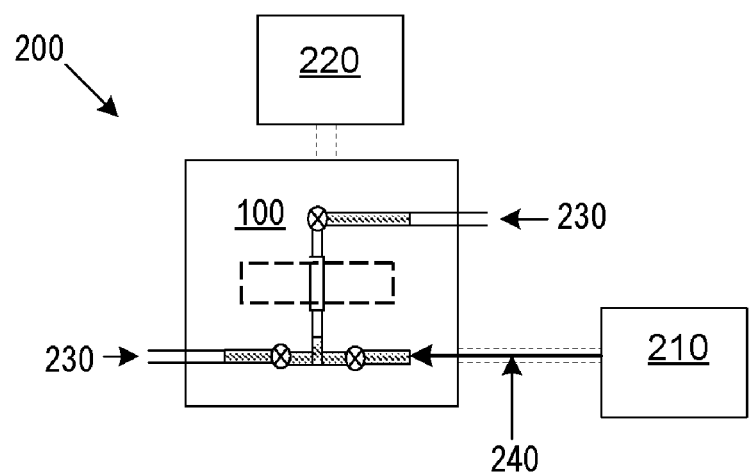
FIG. 2 is a schematic diagram depicting an embodiment of a system for direct detection of one or more markers in a hydrocarbon fluid.

FIG. 2 depicts a schematic drawing of an embodiment of a system for detection of one or more markers in a hydrocarbon fluid. System 200 may include apparatus 100, hydrocarbon fluid source 210, processor 220, and vents 230. In some embodiments, one or more of vents 230 may be coupled to a waste receptacle.

Apparatus 100 may be coupled to hydrocarbon fluid source 210 via connector 120. Hydrocarbon fluid source 210 may include, but is not limited to, a cylinder, a storage tank, a vehicle, transport container, or a conduit. Hydrocarbon fluid 240 may be stored in or transported through hydrocarbon fluid source 210.

Processor 220 may automate all or a portion of direct detection of one or more markers in a hydrocarbon fluid. In some embodiments, processor 220 includes software to operate valves 150, 160, 170 to allow purging, filling, venting, and refilling of vessel 130. In certain embodiments, processor 220 includes software to operate detector 140 together with or separately from valves 150, 160, 170. Processor 220 may be coupled to one or more input and/or display devices to allow a user to specify parameters including, but not limited to, timing of valve opening/closure, timing of detector operation, excitation and/or emission wavelength, data content and/or display format, etc.

In some embodiments, direct detection of one or more markers in a hydrocarbon fluid may include purging the vessel before detection. This may be achieved, for example, by the following steps. Valves 150, 160, and 170 are initially closed. Hydrocarbon fluid source 210 is coupled to conduit 110 via connector 120. A valve on hydrocarbon fluid source 210 is opened to allow hydrocarbon fluid 240 to flow from the hydrocarbon fluid source into apparatus 100. Valve 150 is opened to allow at least partial filling of vessel 130 with hydrocarbon fluid 240. The filling level may depend on the pressure of hydrocarbon fluid 240 in hydrocarbon fluid source 210 and/or the volume of vapor (for instance, air) in vessel 130. Valve 160 is opened to allow hydrocarbon fluid 240 to rise in vessel 130 while the vapor in the vessel is displaced. Valve 160 is closed when vessel 130 is substantially filled with hydrocarbon fluid 240. Valve 150 is then closed to inhibit flow of hydrocarbon fluid 240 from hydrocarbon fluid source 210. Valve 170 can be opened to allow hydrocarbon fluid 240 to escape from vessel 130 and then re-closed.

Vessel 130 may be filled, or at least partially filled, with hydrocarbon fluid 240 to allow direction detection of markers in the hydrocarbon fluid. Again, by way of example of an embodiment of the invention, to fill vessel 130, valve 150 is opened to allow hydrocarbon fluid 240 to flow from hydrocarbon fluid source 210 to vessel 130. Valve 150 may be closed after vessel 130 is filled to a desired level. In an embodiment, valve 150 is closed after vessel 130 is substantially filled with hydrocarbon fluid 240. Detector 140 is operated to assess one or more properties of one or more markers in hydrocarbon fluid 240. In some embodiments, operation of the detector includes irradiating hydrocarbon fluid 240 in vessel 130 to assess the fluorescence of one or more fluorescent markers in the hydrocarbon fluid. Valve 170 can then be opened to allow hydrocarbon fluid 240 (for instance, hydrocarbon liquid) to exit vessel 130 and then re-closed.

With apparatus 100 coupled to hydrocarbon fluid source 210, direct detection may be repeated as desired. In some embodiments, one or more properties of one or more markers in hydrocarbon fluid may be assessed two or more times. Following completion of desired testing, a valve on the hydrocarbon fluid source 210 may be closed to inhibit flow of hydrocarbon fluid 240 from the hydrocarbon fluid source. Valves 150, 160, 170 may be opened to vent apparatus 100. Apparatus 100 may then be uncoupled from hydrocarbon fluid source 210.

In certain embodiments, apparatus 100 may remain coupled to hydrocarbon fluid source 210 for future use. In certain embodiments, detector 140 may be uncoupled from apparatus 100, and the apparatus may remain coupled to hydrocarbon fluid source 210.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An apparatus configured for detecting a marker previously inserted into a pressurized hydrocarbon fluid, comprising:
    a first valve configured to couple to a hydrocarbon fluid source;
    a vessel coupled to the first, valve, wherein the first valve is configured to selectively pass pressurized hydrocarbon fluid from the hydrocarbon fluid source into the vessel; and
    a detector configured to couple to the vessel, wherein the detector is configured to detect a presence or absence of the marker in the pressurized hydrocarbon fluid in the vessel.

2. The apparatus of claim 1, wherein the pressurized hydrocarbon fluid is liquefied petroleum gas.

3. The apparatus of claim 1, wherein the first valve is configured to be coupled to a processor.

4. The apparatus of claim 1, wherein the first valve is coupled to a processor.

5. The apparatus of claim further comprising a second valve, wherein the second valve is coupled to the first valve, and wherein the second valve is configured to release the pressurized hydrocarbon fluid from the apparatus in a liquid state.

6. The apparatus of claim 5, further comprising a third valve, wherein the third valve is coupled to the vessel, and wherein the third valve is configured to release the pressurized hydrocarbon fluid from the apparatus in a gaseous state.

7. The apparatus of claim 1, further comprising a second valve, wherein the second valve is coupled to the vessel, and wherein the second valve is configured to release the pressurized hydrocarbon fluid from the apparatus in a gaseous state.

8. The apparatus of claim 1, wherein the vessel is configured to contain a pressurized hydrocarbon fluid at a pressure of up to about 15 bar.

9. The apparatus of claim 1, wherein the detector is configured to be operatively coupled to the vessel.

10. The apparatus of claim 1, wherein the detector is configured to be physically coupled to the vessel.

11. The apparatus of claim 1, wherein the detector comprises a spectrometer.

12. The apparatus of claim 1, wherein the detector comprises a fluorometer.

13. The apparatus of claim 1, wherein the detector is further configured to detect a quantity of the marker in the pressurized hydrocarbon fluid.

14. The apparatus of claim 1, wherein the apparatus allows direct detection of the marker in the pressurized hydrocarbon fluid.

15. A system comprising:
    a hydrocarbon fluid source comprising a pressurized hydrocarbon fluid, wherein the pressurized hydrocarbon fluid comprises a marker;
    a first valve coupled to the hydrocarbon fluid source;
    a vessel coupled to the first valve, wherein the first valve is configured to allow at least some of the pressurized hydrocarbon fluid in the hydrocarbon fluid source to flow into the vessel; and
    a detector coupled to the vessel, wherein the detector is configured to detect a property of the marker in the pressurized hydrocarbon fluid in the vessel.

16. The system of claim 15, wherein the pressurized hydrocarbon fluid is liquefied petroleum gas.

17. The system of claim 15, wherein the first valve is coupled to the hydrocarbon fluid source.

18. The system of claim 15, wherein the detector is coupled to the vessel.

19. The system of claim 15, wherein the detector comprises a spectrometer.

20. The system of claim 15, wherein the detector comprises a fluorometer.

21. The system of claim 15, further comprising a processor, wherein the processor is coupled to the detector.

22. The system of claim 15, further comprising a processor, wherein the processor is coupled to the first valve.

23. The system of claim 15, wherein the system is configured for direct detection of the marker in the pressurized hydrocarbon fluid.

24. The system of claim 15, wherein the system is configured for direct detection of the marker in the pressurized hydrocarbon fluid using an in-line optical fiber.

25. The system of claim 15, wherein the property of the marker is the presence or absence of the marker.

26. The system of claim 15, wherein the property of the marker is a quantity of the marker in the pressurized hydrocarbon fluid.

27. An apparatus configured to detect a marker in a pressurized hydrocarbon fluid, the marker indicating an origin of the fluid, wherein the apparatus comprises:
    a first valve configured to be coupled to a hydrocarbon fluid source;
    a vessel coupled to the first valve, wherein the first valve is configured to allow pressurized hydrocarbon fluid from the hydrocarbon fluid source to flow into the vessel, and wherein the vessel is configured to be coupled to a detector to allow direct detection of a property of the marker in the pressurized hydrocarbon fluid.

28. The apparatus of claim 27, further comprising a detector operatively coupled to the vessel.

29. The apparatus of claim 27, further comprising a detector physically coupled to the vessel.

30. The apparatus of claim 27, wherein the pressurized hydrocarbon fluid is liquefied petroleum gas.

31. The apparatus of claim 27, wherein the property of the marker is a presence or absence of the marker.

32. The apparatus of claim 27, wherein the property of the marker is a quantity of the marker in the pressurized hydrocarbon fluid.

33. A method of detecting a marker in a pressurized hydrocarbon fluid, comprising:
    coupling a vessel to a hydrocarbon fluid source comprising a pressurized hydrocarbon fluid:
    at least partially filling the vessel with the pressurized hydrocarbon fluid from the hydrocarbon fluid source;
    detecting a property of the marker in the hydrocarbon fluid with a detector while the vessel is coupled to the hydrocarbon fluid source.

34. The method of claim 33, wherein the pressurized hydrocarbon fluid is liquefied petroleum gas.

35. The method of claim 33, wherein at least partially filling the vessel comprises purging air from the vessel.

36. The method of claim 33, wherein detecting comprises coupling the detector to the vessel.

37. The method of claim 33, wherein detecting comprises assessing an amount of the marker in the pressurized hydrocarbon fluid.

38. The method of claim 33, wherein the detector comprises a light source, and wherein detecting comprises illuminating the pressurized hydrocarbon fluid in the vessel with the light source.

39. The method of claim 33, wherein the detector comprises a fluorometer.

40. The method of claim 33, wherein at least partially filling the vessel comprises, controlling a valve coupled to the hydrocarbon fluid source with a processor.

41. The method of claim 33, wherein detecting the property of the marker in the pressurized hydrocarbon fluid with a detector comprises controlling the detector with a processor.

42. The method of claim 33, further comprising decoupling the vessel from the hydrocarbon fluid source.

43. The method of claim 33, wherein the property of the marker is the presence or absence of the marker.

44. The method of claim 33, wherein the property of the marker is a quantity of the marker in the pressurized hydrocarbon fluid.

* * * * *